US00PP09965P

United States Patent [19]

Jack et al.

[11] Patent Number: Plant 9,965

[45] Date of Patent: Jul. 15, 1997

[54] CHAMELAUCIUM (WAXFLOWER) PLANT NAMED 'ROSIE'

[75] Inventors: Brian Jack; Victoria Syme, both of Coorow, Australia

[73] Assignee: New World Plants USA, Escondido, Calif.

[21] Appl. No.: 602,177

[22] Filed: Feb. 20, 1996

[51] Int. Cl.[6] ..... A01H 5/00

[52] U.S. Cl. ..... Plt./54.1

[58] Field of Search ..... Plt./54.1

*Primary Examiner*—James R. Feyrer

*Attorney, Agent, or Firm*—C. A. Whealy

[57] ABSTRACT

A new and distinct interspecific Chamelaucium hybrid cultivar (known commercially as waxflower) distingished by its strong and erect flowering stems; upright and semi-open growth habit; dense terminal floral display; dark ref flower bud color; dark pink flower color; and good postharvest longevity.

3 Drawing Sheets

The present invention relates to a new and distinct cultivar of Chamelaucium (Waxflower), botanically known as an interspecific Chamelaucium hybrid, and hereinafter referred to by the cultivar name Rosie.

The new cultivar is a product of a planned and controlled breeding program conducted by the inventors in Coorow, Western Australia, Australia. The new cultivar originated from a deliberate cross by the inventors between two different species of the genus Chamelaucium. An unnamed selection of *Chamelaucium megalopetalum* was used as the female or seed parent and the *Chamelaucium uncinatum* cultivar Purple Pride (not patented) was used as the male or pollen parent. Twenty days after the cross-pollination, the immature seed pod was harvested and the develping embryos were aseptically dissected and transferred onto a nutrient agar-based medium for further development. Mature plants developed from these dissected embryos. The cultivar Rosie was discovered and selected by the inventors as a flowering plant within the progeny of the stated cross in a controlled environment in Coorow, Western Australia, Australia.

Asexual propagation of the new cultivar by cuttings taken at Coorow, Western Australia, Australia, and Escondido, Calif., has shown that the unique features of this new Chamelaucium plant are stabilized and reproduced true to type in successive generations of asexual propagation.

The following traits have been repeatedly observed and are determined to be the unique characteristics of the new Chamelaucium. These characteristics in combination distinguish Rosie as a new and distinct cultivar:

1. Strong and erect flowering stems.
2. Upright and semi-open growth habit.
3. Dense terminal floral display.
4. Dark red flower bud color.
5. Dark pink flower color.
6. Good postharvest longevity.

The new Chamelaucium differs from its seed parent, the selecton of *Chamelaucium megalopetalum*, in the following characteristics:

1. Plants of the new Chamelaucium flower faster than plants of the seed parent.
2. The petal shape of plants of the new Chamelaucium is round whereas the petal shape of plants of the seed parent is obovate.
3. The flower bud color is darker red on plants of the new Chamelaucium than the flower bud color on plants of the seed parent.
4. At maturity, the petal color of the new Chamelaucium is dark pink whereas the petal color of the seed parent is white.

5. Plants of the new Chamelaucium have more flowers per stem and appear more dense and full than plants of the seed parent.
6. Plants of the new Chamelaucium have broader flowering stems compared to plants of the seed parent.

The new Chamelaucium differs from its pollen parent, the *Chamelaucium uncinatum* cultivar Purple Pride, in the following characteristics:

1. The petal shape of the new Chamelaucium is round whereas the petal shape of Purple Pride is obovate.
2. The petal color of the new Chamelaucium when opening is white compared to the purple petal color of Purple Pride. At maturity, the petal color of the new Chamelaucium is dark and the petal color of Purple Pride is red purple. The flower color development rate is slower for plants of the new Chamelaucium compared to plants of the pollen parent. The floral tube color is also different, as the floral tube of the new Chamelaucium is yellow green and the floral tube of Purple Pride is red brown.
3. Plants of the new Chamelaucium have more flowers per stem and appear more dense and full than plants of Purple Pride.

The new Chamelaucium can be compared to the Chamelaucium cultivar Revelation, disclosed in U.S. Pat. No. P.P. 8,791. Plants of Rosie differ from plants of revelation in the following characteristics:

1. Plants of the new Chamelaucium have shorter internodes, smaller leaves, and longer peduncles than plants of Revelation.
2. The petal color of the new Chamelaucium at maturity is dark pink compared to the light violet petal color of Revelation. The flower color development rate is slower for plants of the new Chamelaucium compared to plants of Revelation.
3. The floral tube color at the distal end is yellow green on plants of the new Chamelaucium and the floral tube color at the distal end is purple brown on plants of Revelation.
4. Plants of the new Chamelaucium have smooth floral tubes compared to the prominently fluted floral tubes of plants of Revelation.

A detailed comparison of the new Chamelaucium, its parents and Revelation plants appears in Chart A at the end of the specification.

The new Chamelaucium plant has not been observed under all possible environmental conditions. The phenotype may vary significantly with variations in environment such as temperature and light level, without, however, any variance in genotype.

The accompanying colored photographs show typical specimens of the vegetative growth and flowers of the new Chamelaucium plant, showing the colors as true as it is reasonably possible to obtain in colored reproductions of this type.

The first photograph comprises a side perspective view of typical flowering stems of the new Chamelaucium plant grown in Escondido, Calif. This photograph shows the upright and semi-open growth habit of flowering stems of the new Chamelaucium.

The second and third photographs comprise close-up views of the new Chamelaucium's flowers showing the cultivar's unique petal colors that change with the development of the flower.

In the second photograph, flower buds are dark red; and as the flowers open, the petal color is white with a slight pale pink blush.

In the third photograph, flowers shown are approaching maturity and petal color is increasingly becoming dark pink in color.

The following observations, measurements, values, and comparisons describe plants grown in Escondido, Calif. Values representing size of plants, flowers and foliage are averages of plants produced under standard commercial cultural practices. Color references are made to The Royal Horticultural Society Colour Chart except where general terms of ordinary dictionary significance are used.

Classification:

*Botanical.*—An interspecific Chamelaucium hybrid, *Chamelaucium megalopetalum* × *Chamelaucium uncinatum* cultivar Rosie.

*Commercial.*—Hybrid waxflower.

Parentage:

*Female or seed parent.*—Selection of *Chamelaucium megalopetalum* (not patented).

*Male of pollen parent.*—*Chamelaucium uncinatum* cultivar Purple Pride (not patented).

Plant description:

*Form.*—Erect, branched woody shrub.

*Growth habit.*—Vigorous, rigid and upright. Semi-open growth habit.

*Flowering stem length.*—1.8 m.

*Foliage description.*—Numerous leaves on one- and two-year-old wood; opposite arrangement; sessile; and aromatic. Internode length: 10 mm. Leaf size: Length: 10 mm. Width: 1 mm. Shape: Narrowly lanceolate. Texture: Glabrous. Margin: Entire. Aspect: Flat and thick. Color: Dark green sometimes with red tint.

Flower description:

*Flowering season.*—Flowers develop and open throughout the spring.

*Flower longevity.*—Flower are long-lasting on the plant and after cutting, flowers and calyx persistent.

*Flowering habit.*—Flowers develop on thin first-year stems from upper axils. Numerous flowers arranged in terminal clusters, broad and dense floral display.

*Flower shape.*—Rounded outline, flattened cup-shaped floral tube with rounded, slightly cupped, orbicular petals.

*Flower diameter.*—1.8 cm.

*Flower bud.*—Form: Spherical, covered with thin deciduous bracteoles. Diameter: 7 to 8 mm prior to petal opening. Color: With operculum: Dark red (46A). Without operculum: White (155D). Bud tube: Green (143C).

*Petals.*—Quantity: Five. Shape: Rounded, slightly cupped and orbicular. Diameter: 8 mm. Texture: Waxy. Calyx: Five calyx lobes arranged alternately between petals. Color: When opening: White (155D) with pale pink blush at times. Developing flowers: White (155D) background with light pink (70D) areas a petal distal ends. Mature flowers: As flowers age, petals become more uiformly dark pink (61C) in color with light violet (75A) venation. Flower nectary, immature: Yellow green (144A). Flower nectary, mature: Yellow green (152A). Calyx lobe, mature: Pale pink/purple. Floral tube: Fluting: Slight to absent. Outline: Flared. Diameter: 8 mm. Color: Midpoint: Yellow green. Distal end: Yellow green. Peduncles: Length: 17 mm. Aspect: Upright and erect. Color: Green. Fragrance: Aromatic when crushed.

*Reproductive organs.*—Stamens: Quantity: Ten fertile stamens with ten infertile stamenoids arranged alternatively between stamens. Staminoidal outline: Narrow to medium, triangular. Stamenoidal collar color, mature: Pale pink to purple. Anthers, mature: Width: 0.7 mm. Color: Brown (200D). Filaments: Length: 2.5 mm. Color: White. Pollen: Color: Green brown. Texture: Waxy and sticky. Pistils: Quantity: One. Style: Length: 7 mm. Color: Immature: White (155D). Mature: Light Violet (84B). Stigma: Color, mature: Yellow (17B). Texture: Bearded and pubescent.

*Fruit.*—Shape: Hemispherical. Form: Three-celled capsule formed by the hardened bas of the persistent calyx.

Disease resistance: No resistance or susceptibility to plant pathogens has been observed.

CHART A

| CHARACTERISTIC | ROSIE | PURPLE PRIDE, pollen parent | *Chamelaucium megapetalum* selection, seed parent | REVELATION |
|---|---|---|---|---|
| FLOWER BUD COLOR, WITH OPERCULUM | Dark red 46A | Dark red 46A | Red 46B | Dark red 46A |
| BUD COLOR, WITHOUT OPERCULUM | White 155D | Pale purple 80A | White 155B | White 155D |
| BUD TUBE COLOR | Green 143C | Green 146A | Light green 145A | Green to violet 144A to 77B |
| PETAL SHAPE, AFTER OPENING | Round | Obovate | Obovate | Round |
| PETAL COLOR, WHEN OPENING | White with slight pink blush 155D | Purple 78A | White 155B | White 155C |
| PETAL COLOR DEVELOPMENT RATE | Slow | Medium | Slow | Fast |
| PETAL COLOR, MATURE | Dark pink 61C | Red purple 59B/59C | White 155D | Light violet 84B |
| FLOWER NECTARY COLOR, IMMATURE | Yellow green 144A | Light brown 177D | Green 148A | Green 146D |
| FLOWER NECTARY COLOR, MATURE | Yellow green 152A | Dark purple 187A | Green 146B/ 146C | Green 147A |

CHART A-continued

| CHARACTERISTIC | ROSIE | PURPLE PRIDE, pollen parent | *Chamelaucium megapetalum* selection, seed parent | REVELATION |
|---|---|---|---|---|
| STAMINOIDAL OUTLINE | Narrow/ medium, triangular | Broad, triangular | Medium, triangular | Narrow, triangular |
| STAMINOIDAL COLLAR COLOR, MATURE | Pale pink/ purple | Pale pink/ purple | White | Very pale pink/purple |
| CALYX LOBE COLOR, MATURE | Pale pink/ purple | Pale pink/ purple | White | Pale purple |
| STYLE COLOR, MATURE | Light violet 84B | Purple | White | Light violet 84B |
| FLORAL TUBE FLUTING, IMMATURE | Slight/ absent | Slight | Slight | Prominent |
| FLORAL TUBE OUTLINE | Flared | Flared | Conical | Flared |

CHART A-continued

| CHARACTERISTIC | ROSIE | PURPLE PRIDE, pollen parent | *Chamelaucium megapetalum* selection, seed parent | REVELATION |
|---|---|---|---|---|
| FLORAL TUBE DIAMETER | 8 mm | 7 mm | 6.8 mm | 6.8 mm |
| FLORAL TUBE COLOR, MIDPOINT | Yellow green | Red/ brown | Green | Green |
| FLORAL TUBE COLOR, DISTAL END | Yellow green | Red/ brown | Green | Purple brown |
| FLOWERING STEM SHAPE | Broad | Broad | Narrow | Broad |

It is claimed:

1. A new and distinct Chamelaucium interspecific hybrid plant named Rosie, as illustrated and described.

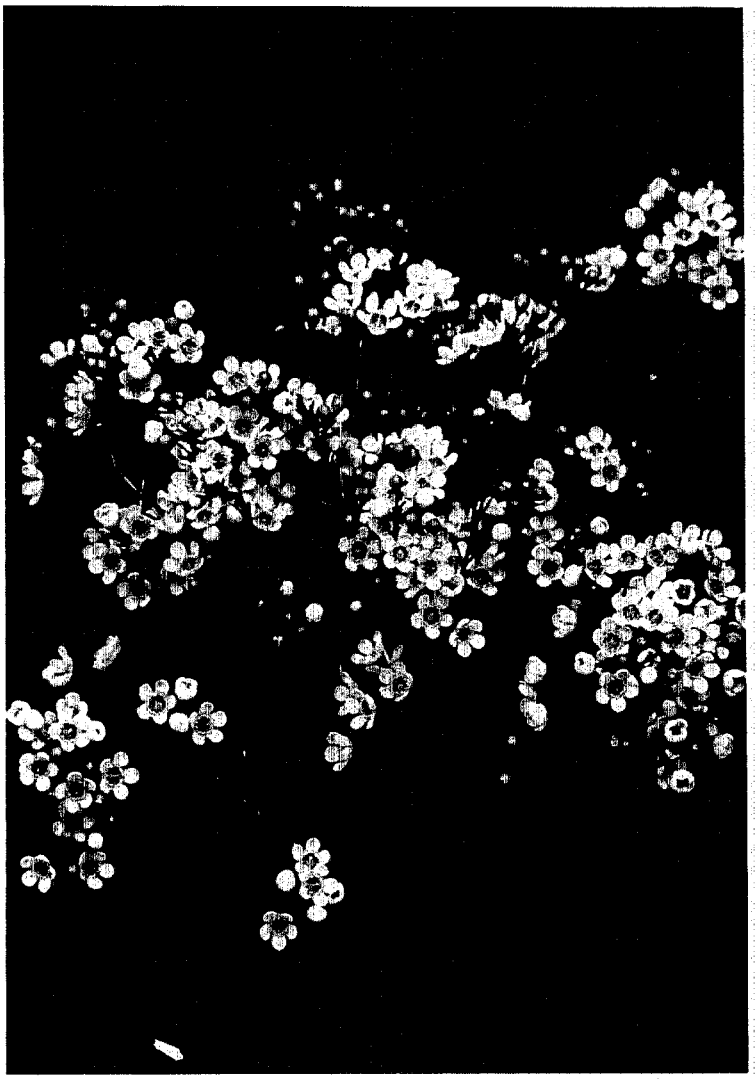

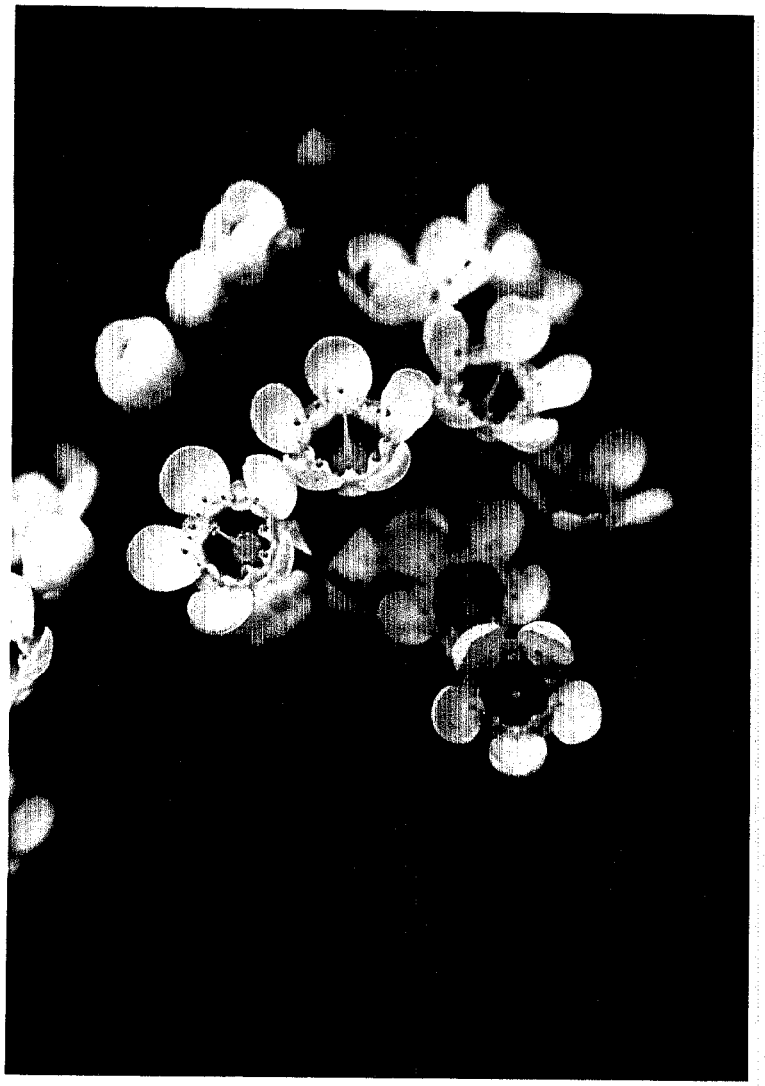

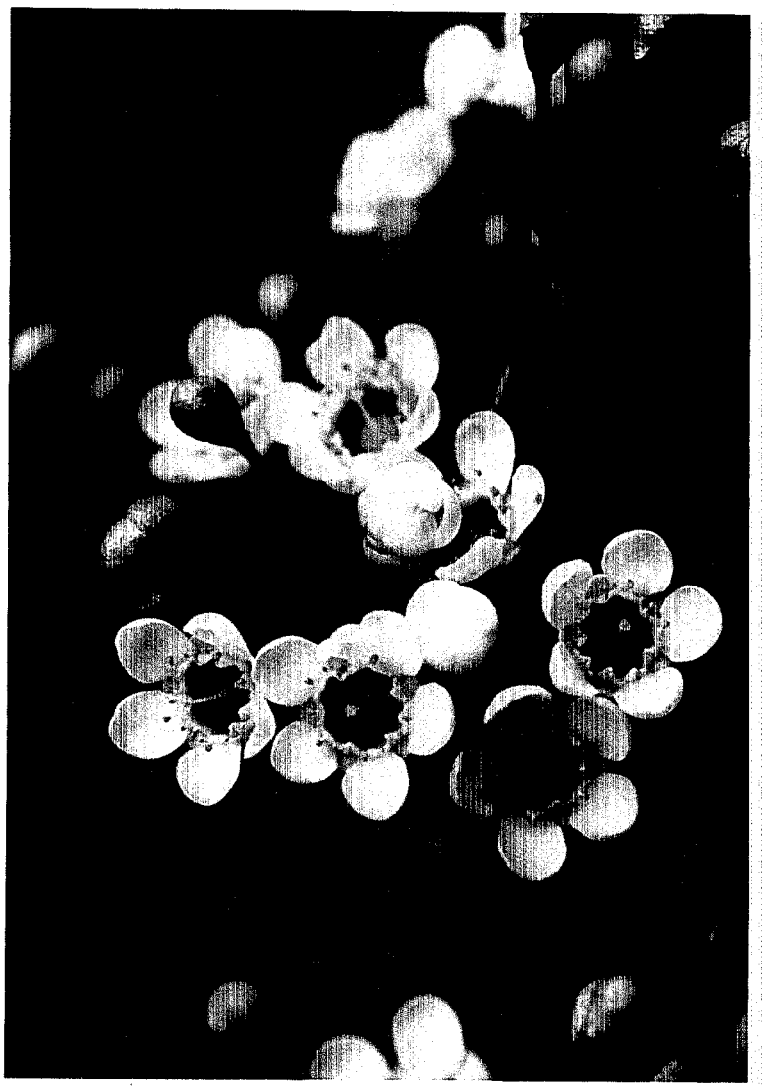

* * * * *